(12) United States Patent
Reynolds et al.

(10) Patent No.: US 12,317,898 B2
(45) Date of Patent: Jun. 3, 2025

(54) ANTIBACTERIAL SURFACE OF METAL-ORGANIC FRAMEWORK-CHITOSAN COMPOSITE FILMS

(71) Applicant: Colorado State University Research Foundation, Fort Collins, CO (US)

(72) Inventors: Melissa M. Reynolds, Fort Collins, CO (US); Megan J. Neufeld, Portland, OR (US); Bella H. Neufeld, Fort Collins, CO (US); Alec Lutzke, Fort Collins, CO (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

Patent file contains an affidavit/declaration under 37 CFR 1.130(b).

(21) Appl. No.: 18/115,789

(22) Filed: Mar. 1, 2023

(65) Prior Publication Data

US 2023/0200395 A1  Jun. 29, 2023

Related U.S. Application Data

(62) Division of application No. 16/630,264, filed as application No. PCT/US2018/041644 on Jul. 11, 2018, now abandoned.

(Continued)

(51) Int. Cl.
*A01N 25/10*  (2006.01)
*A01N 55/02*  (2006.01)
(Continued)

(52) U.S. Cl.
CPC ............ *A01N 55/02* (2013.01); *A01N 25/10* (2013.01); *A61L 2/18* (2013.01); *A61L 2/23* (2013.01);
(Continued)

(58) Field of Classification Search
CPC ...... A01N 59/20; A01N 43/647; A01N 55/02; A01N 25/10; A01N 43/16; A61L 2/18;
(Continued)

(56) References Cited

U.S. PATENT DOCUMENTS

| | | | |
|---|---|---|---|
| 5,648,508 A | 7/1997 | Yaghi | |
| 5,691,423 A | 11/1997 | Smith et al. | |

(Continued)

FOREIGN PATENT DOCUMENTS

| | | |
|---|---|---|
| EP | 2083946 A1 | 8/2009 |
| EP | 2678041 A2 | 1/2014 |

(Continued)

OTHER PUBLICATIONS

Neufeld et al. (ACS Appl. Mater. Interfaces 2017, 9, 5139-5148) (Year: 2017).*

(Continued)

*Primary Examiner* — Ernst V Arnold
(74) *Attorney, Agent, or Firm* — Faegre Drinker Biddle & Reath LLP

(57) ABSTRACT

A substrate having an antibacterial surface includes a chitosan matrix and water-stable metal-organic frameworks dispersed throughout the chitosan matrix. The water-stable metal-organic frameworks are present in an amount of 5% wt/wt to 20% wt/wt based on total solids of the substrate.

11 Claims, 7 Drawing Sheets

Related U.S. Application Data

(60) Provisional application No. 62/531,183, filed on Jul. 11, 2017.

(51) Int. Cl.
*A61L 2/18* (2006.01)
*A61L 2/23* (2006.01)
*C08B 37/08* (2006.01)
*C08K 5/56* (2006.01)
*A61L 101/34* (2006.01)
*A61L 101/42* (2006.01)

(52) U.S. Cl.
CPC .............. *C08B 37/003* (2013.01); *C08K 5/56* (2013.01); *A61L 2101/34* (2020.08); *A61L 2101/42* (2020.08); *A61L 2202/24* (2013.01)

(58) Field of Classification Search
CPC .... A61L 2/23; A61L 2101/34; A61L 2101/42; A61L 2202/24; C08B 37/003; C08K 5/56
See application file for complete search history.

(56) References Cited

U.S. PATENT DOCUMENTS

| | | |
|---|---|---|
| 6,451,337 B1 | 9/2002 | Smith et al. |
| 6,887,485 B2 | 5/2005 | Fitzhugh et al. |
| 7,087,709 B2 | 8/2006 | Stamler et al. |
| 7,128,904 B2 | 10/2006 | Batchelor et al. |
| 7,335,383 B2 | 2/2008 | Meyerhoff et al. |
| 7,425,218 B2 | 9/2008 | Keefer et al. |
| 7,637,983 B1 | 12/2009 | Liu et al. |
| 7,763,283 B2 | 7/2010 | Batchelor et al. |
| 7,829,553 B2 | 11/2010 | Arnold et al. |
| 8,007,857 B1 | 8/2011 | Hossainy |
| 8,771,756 B2 | 7/2014 | Reynolds et al. |
| 8,907,043 B2 | 12/2014 | James et al. |
| 9,034,355 B2 | 5/2015 | Reynolds et al. |
| 9,493,352 B2 | 11/2016 | Reynolds et al. |
| 10,266,408 B2 | 4/2019 | Reynolds et al. |
| 2001/0041184 A1 | 11/2001 | Fitzhugh et al. |
| 2002/0115559 A1 | 8/2002 | Batchelor et al. |
| 2002/0119115 A1 | 8/2002 | Keefer et al. |
| 2004/0087510 A1 | 5/2004 | Garvey et al. |
| 2004/0224868 A1 | 11/2004 | Meyerhoff et al. |
| 2005/0220756 A1 | 10/2005 | Stamler et al. |
| 2005/0221072 A1 | 10/2005 | Dubrow et al. |
| 2005/0265958 A1 | 12/2005 | West et al. |
| 2006/0153795 A1 | 7/2006 | West et al. |
| 2007/0014829 A1 | 1/2007 | Batchelor et al. |
| 2007/0286840 A1 | 12/2007 | Arnold et al. |
| 2008/0069863 A1 | 3/2008 | Peters |
| 2008/0220048 A1 | 9/2008 | Chen et al. |
| 2008/0226686 A1 | 9/2008 | Meyerhoff et al. |
| 2008/0255101 A1 | 10/2008 | Garvey et al. |
| 2008/0306012 A1 | 12/2008 | Hrabie et al. |
| 2009/0081279 A1 | 3/2009 | Jezek et al. |
| 2009/0118819 A1 | 5/2009 | Merz et al. |
| 2010/0285100 A1 | 11/2010 | Balkus et al. |
| 2011/0159116 A1 | 6/2011 | Reynolds et al. |
| 2012/0135523 A1 | 5/2012 | James et al. |
| 2014/0017121 A1 | 1/2014 | Schoenfisch et al. |
| 2014/0178504 A1 | 6/2014 | Reynolds et al. |
| 2015/0004257 A1 | 1/2015 | Reynolds et al. |
| 2015/0118268 A1 | 4/2015 | Reynolds et al. |
| 2015/0164821 A1 | 6/2015 | McLaurin |
| 2016/0089444 A1 | 3/2016 | Reynolds et al. |
| 2017/0028390 A1 | 2/2017 | Reynolds et al. |
| 2021/0114011 A1 | 4/2021 | Rubin et al. |
| 2021/0169082 A1 | 6/2021 | Reynolds et al. |

FOREIGN PATENT DOCUMENTS

| | | |
|---|---|---|
| EP | 3651580 A1 | 5/2020 |
| FR | 2929278 A1 | 10/2009 |
| WO | 03/60003 A1 | 7/2003 |
| WO | 2008/020218 A1 | 2/2008 |
| WO | 2008/062160 A1 | 5/2008 |
| WO | 2012/116177 A2 | 8/2012 |
| WO | 2013/006458 A1 | 1/2013 |
| WO | 2013/138073 A1 | 9/2013 |
| WO | 2015/164821 A1 | 10/2015 |
| WO | 2019/014348 A1 | 1/2019 |

OTHER PUBLICATIONS

Nichols et al. (Biomat. Sci. 2013;1:1151-1159). (Year: 2013).*
Seone et al. Chem. Soc. Rev., 2015, 44, 2421-2454). (Year: 2015).*
Kitagawa, Susumu et al., "Functional Porous Coordination Polymers", Angew. Chem. int. Ed 2004, 43, 2334-2375.
Li, H. et al., "Design and Sythesis of an exceptionally stable and highly porous metal organic framework", Nature 1999, vol. 402, pp. 276-279.
Liu et al. "Preparation and characterization of an improved Cu2+-cyclen polyurethane material that catalyzes generation of nitric oxide from S-nitrosothiols", J Mater Chem. Jan. 1, 2012; 22(36): 18784-18787.
Lu et al. (ACS Appl. Mater. Interfaces 2016, 8, 16533-16539). (Year: 2016).
McKinlay, Alistair C. et al., "Exceptional Behavior Over the Whole Adsorption Storage Delivery cycle for NO in Porous Metal Organic Frameworks", Journal of the American Chemical Society, vol. 130, 2008, pp. 10440-10444.
Mekahlia et al., "Chitosan-Copper (II) complex as antibacterial agent: synthesis, characterization and coordinating bond-activity correlation study", Physics Procedia, vol. 2, No. 3, 2009, pp. 1045-1053.
Neufeld et al. "Metal-Organic Framework Material Inhibits Biofilm Formation of Pseudomonas aeruginosa", Advanced Functional Materials, vol. 27, Sep. 13, 2017.
Neufeld et al. "Metal-Organic Framework/Chitosan Hybrid Materials Promote Nitric Oxide Release from S-Nlitrosoglutathione in Aqueous Solution" ACS Applied Materials & Interfaces. Feb. 2, 2017 (Feb. 2, 2017) vol. 9, p. 5139-5148; p. 5139, abstract, left col., para 1, p. 5140. left col., para 1, right col., para 1, p. 5142, left col., para4, p. 5143, left col., para 1, p. 5145, right col., para 3.
Nguyen, J. G. et al., "Moisture-Resitant and Superhydrophobic Metal-Organic Frameworks Obtained via Postsynthetic Modification", Journal of the American Chemical Society, 2010, 132, 4560-4561.
Noble, D. R. et al., "Structure Reactivity Studies of the Cu2 plus catalyzed Decomposition of Four S Nitrosothiols Based around the S NitrocysteineS Nitrosoglutathione Structures", Nitric Oxide: Biology and Chemistry, 2000, 4 (4), 392-398.
Oh, B. K. et al., "Spontaneous Catalytic Generation of Nitric Oxide from S-Nitrosothiols at the Surface of Polymer Films Doped with Lipophilic Copper(II) Complex", Journal of the American Chemical Society, 2003, 125, 9552-9553.
Palmer, R.M.J. et al., "Vascular endothelial cells synthesize nitric oxide from L-arginine", Nature, vol. 333, Jun. 16, 1988, pp. 664-666.
Parola, S., et al. (2016). Optical Properties of Hybrid Organic-Inorganic Materials and their Applications. Adv. Funct. Mater., 26:6506-6544.
Prakash, M. Jaya et al., "Metal-organic macrocycles, metal-organic polyhedra and metal-organic frameworks", Chem. Commun., 2009, 3326-3341.
Puiu, S. C. et al., "Metal Ion-Mediated Nitric Oxide Generation From Polyurethanes via Covalently linked CopperII Cyclen Moieties", Journal of Biomedical Materials Research Part B Applied Biomaterials, 2009, 203-212.
Qiu, Shilun et al., "Molecular engineering for synthesizing novel structures of metal-organic frameworks with multifunctional properties", Coordination Chemistry Reviews 253 (2009) 2891-2911.
Schlichte, K. et al., Improved Synthesis, thermal stability and catalytic properties of the metal organic framework compound Cu3BTC2, Micropourous and Mesoporous Materials, 2004, 73, 81-88.

(56) References Cited

OTHER PUBLICATIONS

Seabra, Amedea B. et al., "Nitric Oxcide-Releasing vehicles for Biomedical Applications", Journal of Materials Chemistry, published 2010, 20, pp. 1624-1637.
Shah, S. U., et al. Synthesis and Characterization of S-Nitrosoglutathione-Oligosaccharide-Chitosan as a Nitric Oxide Donor. Expert Opinion on Drug Delivery, 12(8):1209-1223, Mar. 24, 2015.
Shin et al. Improving the biocompatibility of in vivo sensors via nitric oxide release, The Analyst, 2006, 131, pp. 609-615.
Smith, D. J. et al., "Nitric Oxide releasing polymers Containing the [N(O)NO] Group", Journal of Medicinal Chemistry, 1999, 39, 1148-1156.
Soni, S. D., et al. Nitric Oxide-Releasing Polymeric Microspheres Improve Diabetes-Related Erectile Dysfunction. J. Sex. Med., 10:1915-1925, 2013.
Tanabe, K. K. et al., "Systematic Functionalization of a Metal Organic Framework via a Postsynthetic Modification Approach", Journal of the American Chemical Society, 2008, 130, 8508-8517.
Third Party Observations issued in EP Application No. 10 80 3195.6, mailed Jul. 13, 2015, 3 pages.
Trafton, Anne; Nitric Oxide shown to cause colon cancer, MIT News, 2009, (http://newsoffice.mit.edu/2009/colon-cancer-0119).
Wang, Z. et al., "Post Synthetic Modification of Metal Organic Frameworks", Chemical Society Reviews, 2009, 38, 1315-1329.
Williams, L. H. et al., "The Chemistry of S-Nitrosothiols", Accounts of Chemical Research, 1999, 32, 869-876.
Xiao, Bo et al., "High Capacity Hydrogen and Nitric Oxcide Adsorption and Storage in a Metal-Organic Framework", Journal American Chemical Society, vol. 129, No. 5, 2007, pp. 1203-1209.
Yaghi, O. M. et al., "Reticular Synthesis and the Design of new Materials", Nature 2003, vol. 423, pp. 705-714.
Yaghi, O. M. et al., "Synthetic Strategies, Structure Patterns, and Emerging Properties in the Chemistry of Modular Porous Solids", Accounts of Chemical Research 1998, vol. 31 No. 8, pp. 474-484.
Abdelhameed, R. M. (2014). Post-synthetic modification of metal-organic frameworks. University of Aveiro, Department of Chemistry, 232 pages.
Allendorf, Mark D. et al., "Plasmonic Devices and Sensors Built from Ordered Nanoporous Materials", Sandia Report, SAND2009-5964, Unlimited Release, Printed Sep. 2009, Sandia National Laboratories, 40 pages.
Alsadoni, H. H., "S-Nitrosothiols as Nitric Oxide-Donors: Chemistry, Biology and Possible Future Theraputic Applications", Current Medicinal Chemistry 2004, 11, 2679-2690.
Andrew L. Hook et al., "Discovery of Novel Materials with Broad Resistance to Bacterial Attachment Using Combinatorial Polymer Microarrays", Advanced Materials 2013, 25, pp. 2542-2547, wileyonlinelibrary.com.
Askew, S. C. et al., "Catalysis by Cu2+ of nitric oxide release from S-nitrosothiols (RSNO)", Journal of the Chemical Society Perkin Transaction 2, 1995, 8, 741-745.
Bordiga, S. et al., "Adsorption Properties of HKUST-1 Toward Hydrogen and Other Small Molecules Monitored by IR", Physical Chemistry Physics, vol. 9, 2007, pp. 2676-2685.
Britt, David et al., "Ring-Opening Reactions Within Porous metal—Organic Frameworks", Inorg. Chem. 2010, 49, 3387-6389.
Chen, Banglin et al., "A Microporous Metal-organic Framework for Gas-Chromatographic Separation of Alkanes", Angew. Chem. 2006, 118, pp. 1418-1421.
Chui, S. et al., "A Chemically Functionalizable Nanoporous Material Cu3TMA2H2O3", Science 1999, vol. 283, pp. 1149-1150.
Dahm, Christina C.; et al. "Persistent S-Nitrosation of Complex I and Other Mitochondrial Membrane Proteins by S-vlitrosothiols but Not Nitric Oxide or Peroxynitrite." Journal of Biological Chemistry, 281 (15): 10056-10065, Apr. 14, 2006.
Damodaran, Vinod Babu et al., "Conformational Studies of Covalently Grafted Polyethylene Glycol) on Modified Solid Vlatrices Using X-ray Photoelectron Spectroscopy", Langmuir 2010, vol. 26, No. 10, pp. 7299-7306.

Demessence, A. et al., "Strong CO2 Binding in a Water-Stable, Triazolate-Bridged Metala Organic Framework runctionalized with Ethylenediamine", Journal of the American Chemical Society, 2009, 131 (25), 8784-8786.
Dicks, A. P. et al., "Decomposition of S-nitrosothiols: the effects of added thiols", Journal of the Chemical Society 3erkin Transactions 1997, pp. 1429-1434.
Dicks, A. P. et al., "Generation of nitric oxide from S-nitrosothiols using protein bound Cu2+ sources", Chemistry & Biology 1996, vol. 3, 655-659.
Dicks, Andrew P. et al., "Identification of Cu as the effective reagent in nitric oxide formation from S-nitrosothiols (RSNO)", J. Chem. Soc., Perkin Trans. 2, 1996, pp. 481-487.
Dinca et al., Observation of Cu2—H2 Interactions in a Fully Desolvated Sodalite-Type Metal-Organic Framework, Angewandte Chem., Int. Ed., 2007, 46, pp. 1419-1422.
Drago, R. S. et al., "The Reaction of Nitrogen (II) Oxide with Diethylamine", Journal of the American Chemical Society, 1960, 82, 96-98.
Drago, R.S. et al., "The Reaction of Nitrogen (II) Oxide with Various Primary and Secondary Amines", Journal of the American Chemical Society, 1961, 83, 1819-1822.
Eddaoudi, M. et al., "Modular Chemistry: Secondary Building Units as a Basis for the Design of Highly Porous and Robust Metal Organic Carboxylate Frameworks", Acc. Chem. Res., 2001, 34, 319-330.
Ellman, George L., "Tissue Sulfhydryl Groups", Archives of Biochemistry and Biophysics vol. 83, 70-77 (1959).
Ene, Cristian D. et al., "One-dimensional and two-dimensional coordination polymers constructed from copper(II) nodes and polycarboxylato spacers: synthesis, crystal structures and magnetic properties", Polyhedron 27(2008) 574-582.
Extended European Search Report issued in EP Application No. 12749029.0, mailed Nov. 19, 2015, 11 pages.
Fleser, P. S. et al., "Nitric oxide-releasing biopolymers inhibit thrombus formation in a sheep model of arteriovenous )ridge grafts", Journal of Vascular Surgery 2004, vol. 40 No. 4, 803-811.
Frost, M. C. et al., "Polymers Incorporating Nitic Oxide Releasing/ Generating Substances for Improved Biocompatibility of Blood-Contacting Medical Devices", Biomaterials 2005, 26, 1685-1693.
Frost, Megan C. et al., "Synthesis, Characterization, and Controlled Nitric Oxide Release from S-Nitrosothiol-Derivatized Fumed Silica Polymer Filler Particles", Copyright 2005, Wiley Periodicals, Inc., pp. 409-419.
Furuyama, Shozo et al., "Physisorption of Nitric Oxide, Carbon Monoxide, Nitrogen, and Oxygen by Magnesium Oxide Powder", The Journal of Physical Chemistry, vol. 28, No. 9, 1978, pp. 1028-1032.
Garibay, Sergio J. et al., "Postsynthetic Modification: A Versatile Approach Toward Multifunctional Metal-Organic Frameworks", Inorg. Chem. 2009, 48,7341-7349.
Harding et al., "A tunable, stable and bioactive MOF catalyst for generating a localized therapeutic from endogenous sources", Adv. Func. Mater., vol. 24, 2014, pp. 7503-7509.
Harding, Jacqueline L. et al., "Metal Organic Frameworks as Nitric Oxide catalysts", J. Am. Chem. Soc. 2012, 134(7), pp. 3330-3333.
Hart, T. W., "Some Observations Concerning the S-nitroso and S-phenylsulphonyl Derivatives of L-cysteine and Glutathione", Tetrahedron Letters 1985, 26 (16), 2013-2016.
Herm, Zoey R. et al., "Metal-Organic Frameworks as Adsorbents for Hydrogen purification and precombustion Carbon Dioxide Capture", Journal of the American Chemical Society, 2011, vol. 133, pp. 5664-5667.
Horcajada, P., et al. (2006). Metal-Organic Frameworks as Efficient Materials for Drug Delivery. Angew. Chem. Int. Ed., 45:5974-5978.
Hrabie, J. A. et al., "New Nitric Oxide Releasing Zwitterions Derived from Polyamines", Journal of Organic Chemistry 1993, 58, 1472-1476.
http://www.plasticfantasticlibrary.com/library/plastic/156/ polyoxybenzylmethylenglycolanhydride.html, "Plastic Fantastic Library Entry for polyoxybenzylmethylenglycolanhydride (Bakelite)" Accessed Aug. 1, 2018, no pagination.

(56) References Cited

OTHER PUBLICATIONS

Ignarro, Louis J. et al., "Nitric Oxcide Donors and Cardiovascular Agents Modulating the Bioactivity of Nitric Oxide: An Dverview", Cirrulation Research, Jan. 2002, 90, pp. 21-28.

Ingleson, Michael J. et al., "Nitric Oxide Chemisorption in a Postsynthetically Modified metal—Organic Framework", Inorg. Chem. 2009, 48, 9986-9988.

International Preliminary Report on Patentability issued in PCT/US2012/026317, completed Mar. 18, 2014, 6 pages.

International Preliminary Report on Patentability issued in PCT/US2018/027167, mailed Oct. 24, 2019, 10 pages.

International Preliminary Report on Patentability received for PCT Patent Application No. PCT/US10/62229, mailed on Jul. 12, 2012, 7 pages.

International Preliminary Report on Patentability received for PCT Patent Application No. PCT/US2018/027167, mailed on Oct. 24, 2019, 10 pages.

International Preliminary Report on Patentability received for PCT Patent Application No. PCT/US2018/041644, mailed on Jan. 23, 2020, 6 pages.

International Search Report and Written Opinion issued in PCT/US2010/062229, mailed Apr. 15, 2011, 9 pages.

International Search Report and Written Opinion issued in PCT/US2012/026317 mailed Dec. 6, 2012, 10 pages.

International Search Report and Written Opinion issued in PCT/US2018/027167, mailed Jul. 6, 2018, 12 pages.

International Search Report and Written Opinion issued in PCT_US 18_41644, mailed Oct. 30, 2018, 11 Pages.

International Search Report and Written Opinion received for PCT Patent Application No. PCT/US10/62229, mailed on Apr. 15, 2011, 9 pages.

International Search Report and Written Opinion received for PCT Patent Application No. PCT/US2018/027167, mailed on Jul. 6, 2018, 11 pages.

International Search Report and Written Opinion received for PCT Patent Application No. PCT/US2018/041644, mailed on Oct. 30, 2018, 6 pages.

Isaeva, V.I. et al., "The Application of Metal-Organic Frameworks in Catalysis (Review)", Petroleum Chemistry, 2010, vol. 50, No. 3, pp. 167-180.

James, S. L. et al. et al., "Metal Organic frameworks", Chemical Society Reviews, 2003, 32, 276-288.

\* cited by examiner

ANTIBACTERIAL SURFACE OF METAL-ORGANIC FRAMEWORK-CHITOSAN COMPOSITE FILMS

CROSS-REFERENCE TO RELATED APPLICATION

This application is a Divisional Application of U.S. patent application Ser. No. 16/630,264, filed Jan. 10, 2020, which is a U.S. 371 National Stage Application of International Application No. PCT/US2018/041644, filed Jul. 11, 2018, which claims priority to U.S. Provisional Application No. 62/531,183, filed Jul. 11, 2017, all of which are herein incorporated by reference in their entireties.

STATEMENT REGARDING FEDERALLY SPONSORED RESEARCH OR DEVELOPMENT

This invention was made with government support under a NSF CAREER Award (award number 1352201) awarded by the National Science Foundation. The government may have certain rights in the invention.

BACKGROUND

The prevalence of antibiotic resistant bacteria poses a serious threat to human health, leading to increased and prolonged bacterial infections. While bacteria in the free-floating, planktonic state remain susceptible to traditional antibiotics, the vast majority of bacteria exist in the biofilm state, where many antimicrobial agents are less effective. The Gram-negative bacterium *Pseudomonas aeruginosa* (*P. aeruginosa*) is one particularly concerning bacterial strain due to its capacity to rapidly and efficiently form biofilms as well as its inherent ability to develop resistance to antibiotics. The biofilm life cycle is considered to occur in five stages, with the first two steps consisting of reversible and irreversible attachment of planktonic bacteria onto a surface. Therefore, identifying a material with the inherent properties to ultimately repel or reduce the bacterial adhesion of harmful pathogens represents a promising direction for controlling biofilm formation.

SUMMARY

Example 1 is a substrate having an antibacterial surface. The substrate includes a chitosan matrix and water-stable metal-organic frameworks dispersed throughout the chitosan matrix. The water-stable metal-organic frameworks are present in an amount of 5% wt/wt to 20% wt/wt based on total solids of the substrate.

In Example 2, the substrate of Example 1, wherein the water-stable metal-organic frameworks are copper-based, water-stable metal organic frameworks.

In Example 3, the substrate of Example 1, wherein the water-stable metal-organic frameworks are $H_3[(Cu_4Cl)_3-(BTTri)_8]$ ($H_3BTTri=1,3,5$-tris(1H-1,2,3-triazol-5-yl)benzene).

In Example 4, The substrate of Example 1, wherein the water-stable metal-organic frameworks are crystalline after 72 hours in a nutrient broth media.

In Example 5, the substrate of Example 1, wherein the substrate is a biomedical substrate.

In Example 6, the substrate of Example 1, wherein the water-stable metal-organic frameworks present in an amount of 5% wt/wt based on total solids of the substrate.

In Example 7, a method of making a substrate having an antibacterial surface includes dispersing water-stable metal-organic frameworks in a chitosan matrix to form a water-soluble chitosan/water-stable metal-organic framework material, the water-stable metal-organic frameworks present in the water-soluble chitosan/water-stable metal-organic framework material in an amount of 5% wt/wt to 20% wt/wt based on total solids of the material, and converting the water-soluble chitosan/water-stable metal-organic framework material to a water-insoluble chitosan/water-stable copper-based metal-organic framework material with a buffer solution.

In Example 8, the method of Example 7, wherein the water-stable metal-organic frameworks are copper-based, water-stable metal organic frameworks.

In Example 9, the method of Example 7, wherein the water-stable metal-organic frameworks are $H_3[(Cu_4Cl)_3-(BTTri)_8]$ ($H_3BTTri=1,3,5$-tris(1H-1,2,3-triazol-5-yl)benzene).

In Example 10, the method of Example 7, wherein the water-stable metal-organic frameworks are crystalline after 72 hours in a nutrient broth media.

In Example 11, the method of Example 7, and further comprising forming the water-insoluble chitosan/water-stable copper-based metal-organic framework material into a biomedical device.

In Example 12, the method of Example 7, wherein the water-stable metal-organic frameworks present in an amount of 5% wt/wt based on total solids of the substrate.

In Example 13, a method of using a material to reduce adhesion of bacteria on a surface of the material includes exposing the material comprising copper-based metal-organic frameworks dispersed throughout a chitosan matrix to a solution containing the bacteria, wherein during the exposure the material reduces bacterial adhesion by at least 85% in the first six hours of exposure as compared to material that does not include the copper-based metal-organic frameworks and wherein after the first six hours of exposure the material does not release copper in a bactericidal effective amount.

In Example 14, the method of Example 13, and further including removing the material from exposure to the bacteria, sterilizing the material after the removing step, and exposing the material to a new environment of bacterial after the sterilizing step, wherein during the second exposing step the material reduces bacterial adhesion by at least 85% in the first six hours of exposure as compared to material that does not include the copper-based metal-organic frameworks and wherein the material is not subject to regeneration before the second exposing step.

In Example 15, the method of Example 13 wherein the bacteria is *Pseudomonas aeruginosa*.

While multiple embodiments are disclosed, still other embodiments of the present invention will become apparent to those skilled in the art from the following detailed description, which shows and describes illustrative embodiments of the invention. Accordingly, the drawings and detailed description are to be regarded as illustrative in nature and not restrictive.

DETAILED DESCRIPTION

Figure 1A:
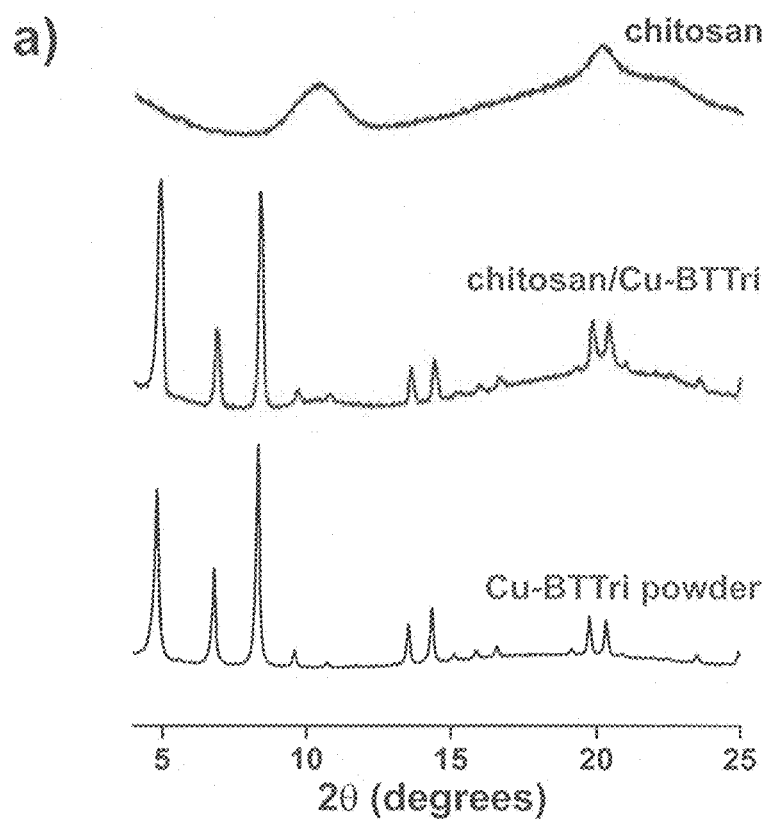
FIG. 1a are powder x-ray diffraction (pXRD) diffraction patterns of chitosan films, chitosan/Cu-BTTri films and Cu-BTTri powder.

Disclosed herein is a substrate material containing chitosan and a water-stable metal-organic framework such as Cu-BTTri ($H_3[(Cu_4Cl)_3$—$(BTTri)_8]$ ($H_3$BTTri=1,3,5-tris(1H-1,2,3-triazol-5-yl)benzene)). In certain embodiments, the material is an antibacterial substrate or film which may be used in biomedical applications. Methods of making the material are also described.

Chitosan is a polysaccharide derived from the biopolymer chitin and has been utilized in multiple biological studies due to its overall biocompatibility and biodegradability. It is composed of β-(1,4)-linked glucosamine and N-acetyl glucosamine units and has been shown to have little to no toxic byproducts. Although there has been emphasis on the antibacterial nature of chitosan in solution against planktonic bacteria, another common use of chitosan as a biomaterial is in the form of wound dressings where it functions as a hemostatic agent. Thrombus formation arising from this type of hemostatic effect may increase the likelihood of biofilm formation, as the adhered proteins onto the chitosan wound dressing provide an ideal area for which bacteria to attach. Therefore, embedding the chitosan matrix with a compound that may improve the materials ability to resist bacterial attachment is one approach to this challenge.

Metal-organic frameworks (MOFs) are a unique class of hybrid materials combining metal centers with organic linkers to produce materials with high porosity. Variation of the metal and ligand has large effects on the overall properties and, therefore, applications of MOFs. While these materials have been widely exploited in gas storage and catalysis, there are fewer studies utilizing MOFs in biological settings. The known biocidal activity of copper has led to some investigation of copper-based MOFs in biological settings for use as potential antibacterial agents. For example, a small number of initial bacteria studies have been carried out using the copper-based MOF copper(II) benzene-1,3,5-tricarboxylate (also known as Cu-BTC or HKUST-1) as an antibacterial agent, attributing the observed biocidal effects to metal sites and the slow, continuous leaching of copper ions, as this MOF undergoes substantial and immediate degradation in aqueous systems. These particular studies did not evaluate bacterial attachment onto MOF-containing surfaces, but rather the biocidal activity of the MOF against planktonic bacteria in solution by copper ions released from the framework. Indeed, copper leaching into bacterial solution has significant antibacterial effects, however in certain embodiments, it is desirable to develop a material that intrinsically prevents the attachment of bacteria without the need for a biocide-eluting surface.

The material disclosed herein includes water-stable MOFs. For example, in some embodiments the MOF remains crystalline and intact after 72 hours in a nutrient broth media as part of a 24-hour bacterial attachment experiment as described herein. In some embodiments, the water-stable MOFs are copper-based. Cu-BTTri ($H_3[(Cu_4Cl)_3$—$(BTTri)_8]$($H_3$BTTri=1,3,5-tris(1H-1,2,3-triazol-5-yl)benzene)) is an exemplary water-stable MOF. CuBTTri is formed of $[Cu_4Cl]^{7+}$ square planar units bound to BTTri$^{3-}$ ligands. Each triazolate ligand interacts with six copper sites on $[Cu_4Cl]^{7+}$ units. CuBTTri has increased metal-ligand bond strength compared to other copper carboxylate MOFs, which confers greater water stability.

The water-stable MOF is incorporated in chitosan. The water-stable MOF can be dispersed throughout the chitosan matrix. The material is denoted as chitosan/water-stable MOF throughout this text, and chitosan/Cu-BTTri when the water-stable MOF is CuBTTri.

In some embodiments, the water-stable MOF is present at 5% wt/wt to 10% wt/wt or 20% wt/wt (based on total solids of the material). In some embodiments, the water-stable MOF is present at 5% wt/wt (based on total solids of the material).

The antibacterial activity of water instable copper-based MOFs has been studied. In such systems, the antibacterial activity can be attributed to the presence of leached copper in in solution. In contrast, the antibacterial activity achieved using a water-stable, copper-based MOF presents a more passive approach to a MOF-polymer antibacterial surface. and the antibacterial activity of the water-stable system cannot be attributed to copper in solution. The water stability of Cu-BTTri and the presence of copper centers makes this MOFs a particularly attractive potential candidate for biological applications.

In some embodiments, the surface of the device is an antibacterial surface that reduces or inhibits bacterial attachment. In some embodiments, the antibacterial surface reduces the bacterial attachment of *Pseudomonas aeruginosa*. Such a device has far-reaching implications, as planktonic bacteria are far more susceptible to antimicrobials and, therefore, less of a concern than biofilm formation.

A method of making a substrate having an antibacterial surface includes dispersing water-stable metal-organic frameworks (MOFs) in chitosan to form a water-soluble chitosan/water-stable metal-organic framework material. The MOFs can be uniformly dispersed throughout the chitosan matrix.

To reduce the likelihood of MOF structural changes arising from exposure to sodium hydroxide, a buffer solution, such as mild pH 8 sodium phosphate buffer solution, can be used to convert the water-soluble chitosan into water-insoluble chitosan.

EXAMPLES

Embodiments of the present invention are further defined in the following non-limiting Examples. It should be understood that these Examples, while indicating certain embodiments of the invention, are given by way of illustration only. From the above discussion and these Examples, one skilled in the art can ascertain the essential characteristics of this invention, and without departing from the spirit and scope thereof, can make various changes and modifications of the embodiments of the invention to adapt it to various usages and conditions. Thus, various modifications of the embodiments of the invention, in addition to those shown and described herein, will be apparent to those skilled in the art from the foregoing description. Such modifications are also intended to fall within the scope of the appended claims. Unless otherwise noted, all parts, percentages, and ratios reported in the following examples are on a weight basis.

Materials

Low molecular weight chitosan (96% deacetylated) and copper(I) iodide (99.5%) were purchased from Sigma-Aldrich (St. Louis, MO, USA). Phosphate buffered saline (PBS) tablets and copper(II) chloride dihydrate were obtained from EMD Chemicals (Gibbstown, NJ, USA). 1,3,5-tribromobenzene (98%), trimethylsilylacetylene (98%), trimethylsilyl azide (94%), diethylamine (99%), were purchased from Alfa Aesar (Ward Hill, MA, USA). Deionized water (18.2 MΩ·cm) was prepared using a Millipore Direct-Q water purification system. Bis(triphenylphosphine)palladium(II) dichloride (98%) was obtained from TCI America (Portland, OR, USA). Chelex-100 Resin was purchased from Bio-Rad (Hercules, CA, USA). *Pseudomonas aeruginosa* (PAO1) was provided by Dr. Brad Borlee at Colorado State University. Oxoidrm nutrient broth media (NBM, OXCM0001B), Oxoid™ nutrient agar (NA, OXCM0003B), and sodium chloride were purchased from Fisher Scientific (Fair Lawn, NJ, USA). CellTiter Blue was purchased from Promega (Madison, WI, USA). Ethanol was purchased from Pharmco-AAPER (Brookfield, CT, USA). 24-well and 96-well tissue culture nontreated plates were obtained from Corning (Corning, NY, USA).

Characterization Techniques

Images were taken at magnification values of 250× and 500× using a JEOL JSM-6500F scanning electron microscope with an accelerating voltage of 10.0 kV and a working distance of 10.1 mm (JEOL USA Inc., MA, USA) equipped with a Thermo Electron energy dispersive X-ray spectrometer (EDX). All samples were dehydrated and coated with 15 nm of Au. All data was processed using TEAM Software. Powder X-ray diffraction (pXRD) measurements were carried out using a Bruker D-8 Discover DaVinci X-ray diffractometer (Bruker, Billerica, MA, USA) with CuKα radiation ($\lambda$=1.5406 Å), and the resulting data was plotted as intensity vs. 2θ in Origin Pro. ATR-IR spectra were recorded in the range of 600-4000 $cm^{-1}$ on a Nicolet 6700 spectrometer (Thermo Electron Corporation, Madison, WI, USA). Elemental analysis was performed using ICP-AES provided by the Colorado State University Soil, Water and Plant Testing Laboratory.

Abbreviations

The following abbreviations are used:
Cu-BTTri=$H_3[(Cu_4Cl)_3$—$(BTTri)_8]$
$H_3$BTTri=1,3,5-tris(1H-1,2,3-triazol-5-yl)benzene Synthesis of $H_3[(Cu_4Cl)_3(BTTri)_8(H_2O)_{12}]\cdot 72H_2O$ (Cu-BTTri-$H_2O$)

The triazole ligand 1,3,5-tris(1H-1,2,3-triazol-5-yl)benzene ($H_3$BTTri) was synthesized following a previously reported protocol by A. Demessence, D. M. D'Alessandro, M. L. Foo, J. R. Long, J. Am. Chem. Soc., 2009, 131, 8784, which is herein incorporated by reference in its entirety. In brief, $H_3$BTTri (225 mg) was suspended in DMF (10 mL) and dissolved at pH 4 following addition of 0.1 M hydrochloric acid. $CuCl_2 \cdot H_2O$ (383 mg) was subsequently added directly to the solution and dissolved, and the resulting mixture was heated in a sealed vessel at 100° C. for 3 days. The reaction produced a violet precipitate (Cu-BTTri-DMF) that was isolated from the supernatant by centrifugation and washed thoroughly with DMF and Millipore water. The MOF was suspended in deionized water and heated at 80° C. for 3 days to exchange DMF, re-isolated by further centrifugation, then washed with Millipore water to yield a light purple powder (Cu-BTTri-$H_2O$). IR: v 3700-3000, 3144, 2953, 1655, 1616, 1534, 1449, 1385, 1358, 1310, 1243, 1226, 1145, 1100, 1024, 979, 885, 830, 775, 689, 678, 664 $cm^{-1}$.

Chitosan Acetate

Chitosan (2.5 g) was suspended in 1% acetic acid (100 mL) and stirred until dissolution. The resulting solution was frozen and lyophilized to obtain water-soluble chitosan acetate.

Chitosan Films

Chitosan acetate (180 mg) was dissolved with Millipore water (6 mL) (3% w $v^{-1}$). The solution was cast into a PTFE mold and the solvent was allowed to evaporate over 48 hours. The resulting chitosan acetate film was removed and suspended in pH 8.0 250 mM sodium phosphate buffer (100 mL). After 15 minutes, the buffer was exchanged and the suspension repeated, after which the film was washed with 5× Millipore water (100 mL). 13 mm diameter films were prepared from the original material and used for subsequent experiments. IR: v 3650-3000, 3355, 3278, 2917, 2849, 1636, 1577, 1542, 1420, 1376, 1321, 1258, 1151, 1056, 1025, 894 $cm^-$.

Chitosan/Cu-BTTri Films

Chitosan/Cu-BTTri films were made having various Cu-BTTri content. Sample films having 20%, 10%, 5% and 1% Cu-BTTri wt/wt (relative to total solids) were formed using the following process. The 10% Cu-BTTri wt/wt films were used in all experiments. The 20%, 5% and 1% sample films were synthesized for bacterial attachment studies. To reduce the likelihood of MOF structural changes arising from exposure to sodium hydroxide, a mild pH 8 sodium phosphate buffer solution was used to convert the water-soluble chitosan acetate into insoluble chitosan.

Chitosan acetate was dissolved in Millipore water (6 mL) according to Table 1. Cu-BTTri was then added according to Table 1, and the viscous mixture was agitated to form a suspension. This suspension was cast into a PTFE mold and allowed to evaporate over 48 hours. The resulting chitosan acetate/Cu-BTTri film was removed and placed in pH 8.0 250 mM sodium phosphate buffer (100 mL). After 15 minutes, the buffer was exchanged and the process repeated, after which the film was washed with 5× Millipore water (100 mL). 13 mm diameter films were punched from the original material and used for subsequent experiments. IR: v 3650-3000, 3356, 3286, 2920, 2854, 1654, 1617 (Cu-BTTri), 1555, 1419, 1376, 1310, 1247, 1227, 1148, 1064, 1023, 892, 826 (Cu-BTTri), 774 (Cu-BTTri) $cm^{-1}$.

TABLE 1

| Sample | Chitosan acetate (mg) | Cu-BTTri (mg) |
|---|---|---|
| 20% wt/wt | 160 | 40 |
| 10% wt/wt | 180 | 20 |
| 5% wt/wt | 190 | 10 |
| 1% wt/wt | 199 | 1 |

Chitosan and Chitosan/Cu-BTTri Cu Content and Soaking Studies

The average copper content of chitosan/Cu-BTTri films was determined by ICP-AES analysis where dissolution of films (n=3) in 1% acetic acid was performed, followed by addition of 37% hydrochloric acid to decompose Cu-BTTri. The 10% wt/wt films were found to contain 295±8 μmol Cu/g. Additional formulations with 1, 5, and 20% Cu-BTTri wt/wt contained 31 f 15, 156±12, and 527±97 µmol Cu/g, respectively. Chitosan films dissolved under identical conditions were found to contain 0.320±0.025 µmol Cu/g. Based on the formula unit of Cu-BTTri-H$_2$O (H$_3$(Cu$_4$Cl)$_3$(BTTri)$_R$(H$_2$O)$_2$·72H$_2$O), the Cu-BTTri content of the final deprotonated 10% films was estimated at 11% wt/wt using the copper content determined by ICP-AES. In the case of 1, 5, and 20% wt/wt films, the estimated Cu-BTTri content was 1, 6, and 20% wt/wt, respectively.

In addition, films were analyzed for residual copper content from synthetic procedure by soaking in NBM at 37° C. for 24, 48, and 72 hours. These solutions were analyzed for elemental analysis using ICP-AES. The resulting copper in solution from the chitosan and chitosan/Cu-BTTri films were determined after subtracting the copper content from the NBM itself under the same conditions. The average copper in solution (mg/L) was normalized for each film by the volume of added NBM (mL) and mass of each film (mg). The percent copper in solution was found by comparing the mass of copper from the soaking solutions over the given soaking periods and the average mass of the total copper content of the films.

The soaking procedure revealed that a range of 0.76-2.47% copper was found in solution (relative to total amount of copper in films). The results from this analysis led to a post-synthetic pre-treatment step where the films were immersed in NBM at 37° C. for 72 hours prior to beginning bacterial attachment assays.

Characterization of Cu-BTTri and Chitosan/Cu-BTTri Films

Figure 1B:
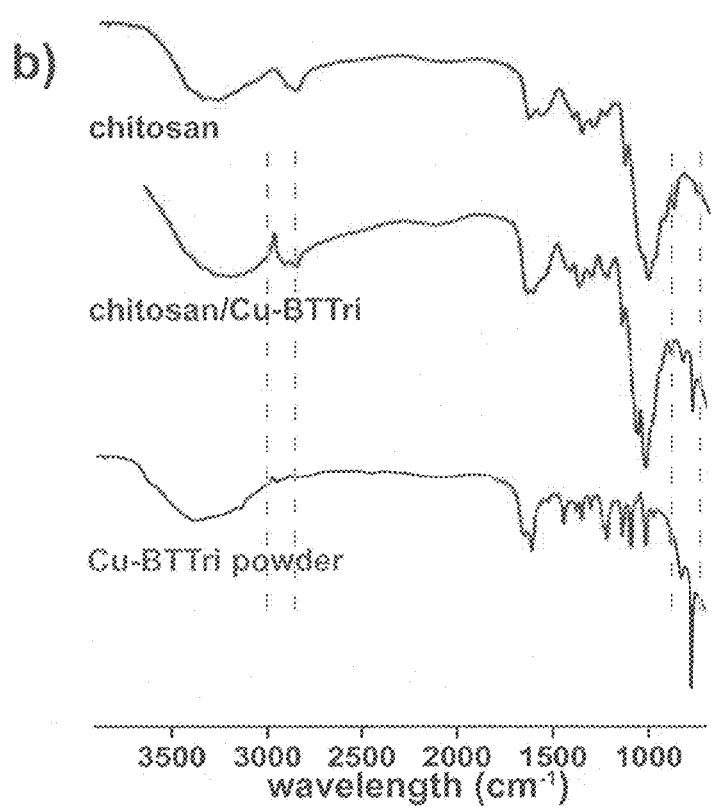
FIG. 1b are attenuated total reflection infrared spectroscopy (ATR-IR) analysis of chitosan films, chitosan/Cu-BTTri films and Cu-BTTri powder.

Cu-BTTri was characterized by pXRD and found to be consistent with the previously reported diffraction pattern. Following the incorporation of the MOF into chitosan, the films were analyzed via pXRD (FIG. 1a) and ATR-IR (FIG. 1b) to ensure that the Cu-BTTri remained structurally intact. The pXRD spectrum of the chitosan/Cu-BTTri films demonstrate the retention of all major diffraction peaks originating from Cu-BTTri with overlaps near 10 and 15-25 2θ that were related to the chitosan material. The ATR-IR spectrum show IR absorptions associated with Cu-BTTri, present at 1617 (aromatic C=C stretch), 830, and 775 cm$^{-1}$ (C—H out-of-plane bending), further supporting successful incorporation of the MOF.

Figure 2A:
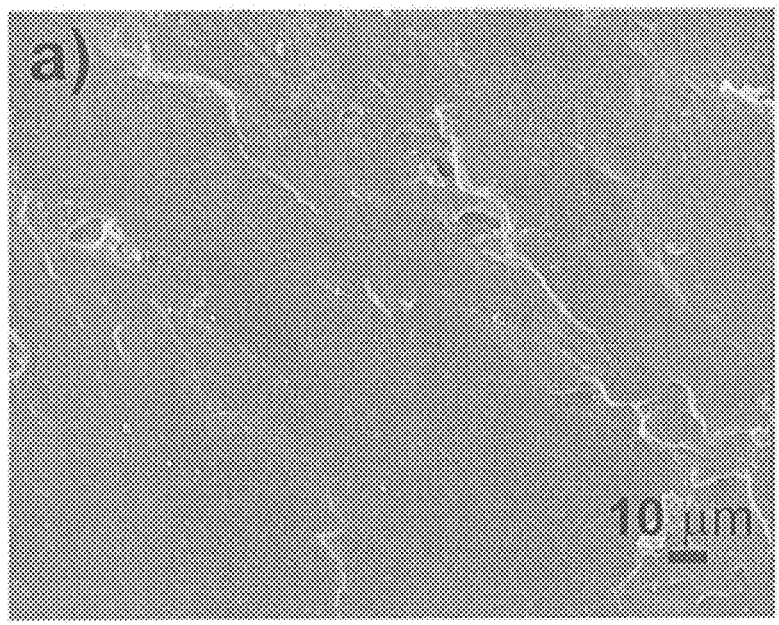
FIG. 2a is a scanning electron microscope (SEM) image of a chitosan film according to some embodiments.
Figure 2B:
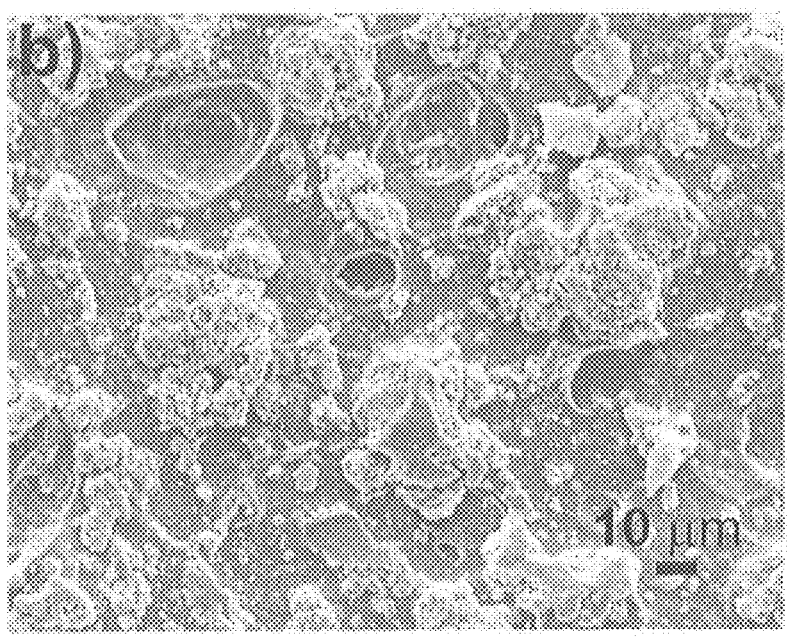
FIG. 2b and FIG. 2c are SEM images of chitosan/Cu-BTTri films according to some embodiments.
Figure 2C:
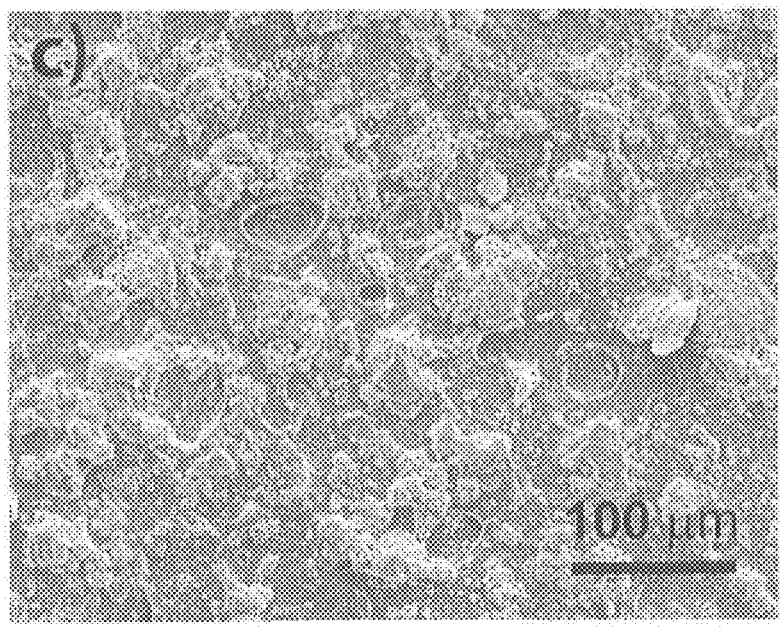
Figure 2D:
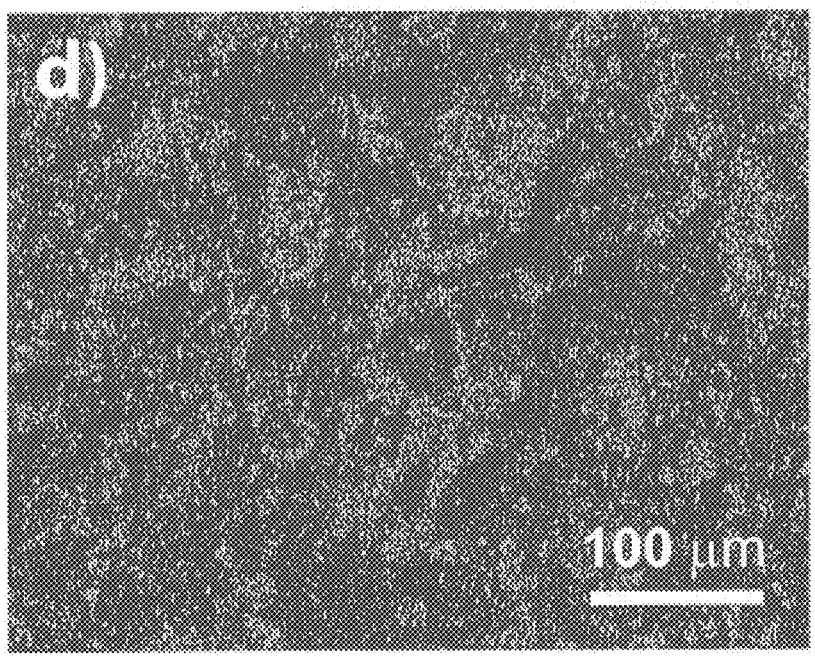
FIG. 2d is an SEM image of the chitosan/Cu-BTTri film with an x-ray analysis (EDX) overlay of copper distribution according to some embodiments.

The chitosan/Cu-BTTri materials were also examined by SEM-EDX to further evaluate the incorporation of Cu-BTTri into the chitosan films. FIG. 2a is a SEM image of a chitosan film; FIGS. 2b and 2c are SEM images of the chitosan/Cu-BTTri film; and FIG. 2d is an SEM image of the chitosan/Cu-BTTri film with an EDX overlay of copper distribution. As shown in FIG. 2b, Cu-BTTri was directly embedded within the chitosan matrix where it is observed that Cu-BTTri is present throughout the entire surface of the film. The material was then evaluated for the overall distribution of copper by SEM-EDX using a copper analysis probe. FIG. 2d shows the copper overlay on the SEM image of the chitosan/Cu-BTTri film, where the overall distribution of copper is generally concentrated in areas that contain crystalline Cu-BTTri.

Bacterial Studies

Currently, there are a number of methods employed to decrease or halt the adhesion step of bacteria onto a surface. The two main approaches are materials that release antibacterial agents and materials with bacteria killing or repelling surfaces. The first method is considered an active approach, where the healthy bacteria are ultimately compromised by exposure to a biocidal agent being released from a material. Conversely, the second approach is considered passive, as there is not a need for a drug-releasing agent, but rather the material contains inherent properties that reduce the amount of adhered bacteria onto that surface (either through contact killing or repelling surfaces). These passive surfaces are particularly attractive for use in biomedical applications because they do not require a reservoir of antibacterial agents and can theoretically be used multiple times. Thus, the chitosan/Cu-BTTri materials were tested to determine if they behave as a passive antibacterial surface.

Additionally, the antibacterial nature of copper-based MOFs has been primarily investigated by exploiting the slow and steady release of copper ions into solution caused by the breakdown of water unstable MOFs. For example, it was previously observed that Cu-BTC grown on silk fibers exhibited high antibacterial action against both *Escherichia coli* (*E. coli*) and *Staphylococcus aureus* (*S. aureus*) planktonic bacteria. In general, copper ions have long been identified as an antibacterial agent, making it evident that copper-based MOFs are breaking down in solution over time and the copper ions are interacting with planktonic bacteria. In contrast, Cu-BTTri, has been shown to be stable in aqueous environments, such as phosphate buffered saline (PBS) and blood. Thus, the utilization of Cu-BTTri allows for the investigation of the potential antibacterial nature of the MOF while eliminating or minimizing activity due to byproducts and possible leachates that could be causing the observed activity on planktonic bacteria.

*Pseudomonas aeruginosa* Bacteria Culture

An initial stock culture of *P. aeruginosa* (PAO1) was obtained by streaking onto agar plates and inoculating a colony in NBM and grown overnight at 37° C. until an O.D.$_{600nm}$~1.0 was reached. This bacterial solution was combined with glycerol (30% v/v) in a 1:1 fashion to obtain a final glycerol concentration of 15% (v/v). These solutions were stored at −80° C. until use. Prior to each bacterial assay, a frozen culture was allowed to thaw and then centrifuged at 4700 rpm for 10 minutes. The supernatant was discarded and the pellet was resuspended using 5 mL NBM. This was transferred to an additional NBM (45 mL) and allowed to grow overnight under stirring conditions until the O.D.$_{600}$=~1.0. The following day, the overnight culture was diluted to an O.D.$_{600}$~0.35 using warmed NBM prior to beginning the attachment assays.

Bacteria Attachment Assays

The ability of chitosan and chitosan/Cu-BTTri films (10% wt/wt) to inhibit bacterial attachment of *P. aeruginosa* over 6- and 24-hour exposure periods was assessed using two bacterial viability assays. This particular bacteria strain is associated with a high level of antibiotic resistance and is one of the most common strains associated with biofilm formation. Due to its ability to quickly form robust biofilms at wound sites, the ultimate goal is to find a material with the capabilities to inhibit the initial attachment of *P. aeruginosa* onto a surface, ultimately preventing the formation of a biofilm. This discovery could have significant impacts on the overall length and severity of bacterial infections. Initial attachment experiments are performed after 6 hours of exposure to a surface, as this is considered the most critical time period after material implantation for biofilm formation to occur. However, it is imperative to ensure that inhibition is maintained over the entire 24-hour challenge period.

Prior to bacteria attachment assays, all films were hydrated overnight using sterile DI water before being transferred to vials containing a mass normalized amount of NBM (1 mL NBM/3.05 mg film) as determined by the leaching assays. The films were stored in NBM at 37° C. for 72 hours. Before being exposed to the bacterial solution, the films were removed from the NBM and placed in a 24-well non-tissue culture treated plate. An aliquot of P. aeruginosa bacterial solution (1 mL) was placed into wells containing the films, with empty wells used as the positive control. The wells were placed in an incubator at 37° C. for either 6 or 24 hours before quantifying the attached bacteria.

A bacteria cellular viability assay was utilized to determine the amount of viable cells on the surface of the films or wells after the exposure period. This was done by removing the bacteria solution from all wells, washing the wells one time with sterilized PBS, moving the films to a new well such that only the bacteria attached to the films and not the surrounding well was assayed, and CellTiter Blue solution (400 µL) was added. The CellTiter Blue solution consisted of 1:5 ratio of CellTiter Blue reagent with NBM. CellTiter Blue exploits the ability of healthy bacteria to convert a blue colored compound resazurin ($\lambda_{max}$=600 nm) to the highly pink compound resorufin ($\lambda_{max}$=570 nm). After addition of the solution, the plate was placed back in the 37° C. incubator for 1-2 hours before 100 µL aliquots were transferred to a 96-well plate and the absorbance was measured at 570 and 600 nm (Synergy 2 Multi-Mode Reader, BioTek, Winooski, Vt., USA). The cellular viability obtained by these absorbance values was normalized for film and well area. (n≥6)

Figure 3A:
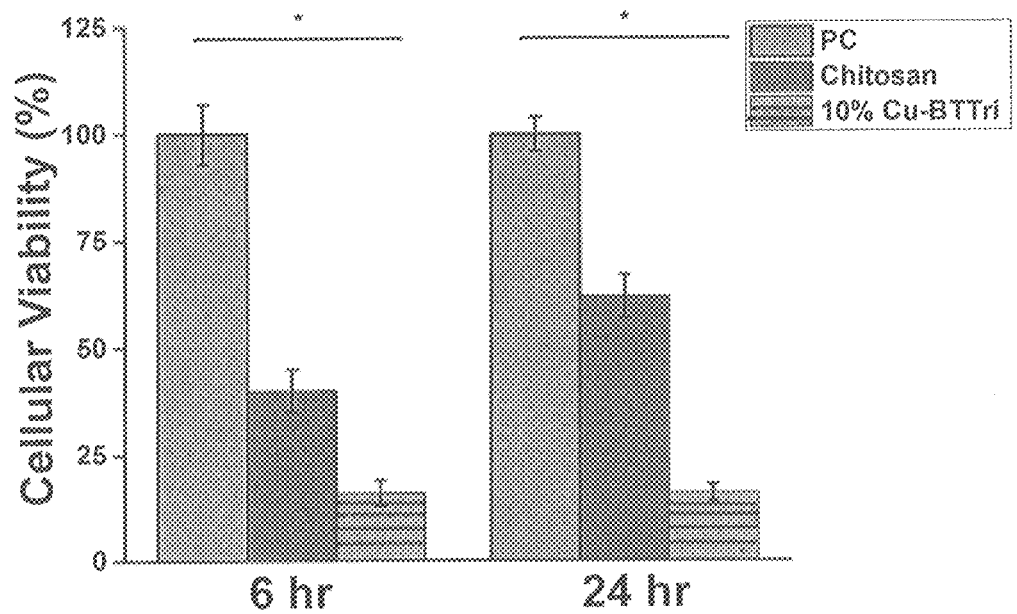
FIG. 3a and FIG. 3b are bar charts reporting cellular viability after 6 hours and 24 hours of exposure according to some embodiments.

By monitoring the absorbance features of both compounds, an overall increase or decrease in metabolic activity of viable bacteria can be assessed by comparison to a positive control. In this case, the positive control (PC) represents non-tissue culture treated polystyrene wells, however, throughout the text the chitosan films without the incorporation of Cu-BTTri will also be utilized and discussed as a positive control, as a further point of comparison. Regardless of the assignment of control wells, bacterial viability was assessed after either 6 or 24 hours and normalized by the given area available for bacteria attachment. FIG. 3a displays the results of this assay, with the polystyrene well as the positive control (PC). After 6 hours of exposure to bacteria, a 55-65% (displayed as the confidence interval) reduction in attachment is seen for the chitosan films, while chitosan/Cu-BTTri films display an even greater reduction of 81-87% in attachment of viable bacteria. Given the established antibacterial properties of chitosan, it is useful to consider the reduction in viable bacteria onto the chitosan/Cu-BTTri when compared to the chitosan itself as a positive control. This results in a 50-68% reduction in attachment after the 6-hour period. This is a significant reduction to achieve in a 6-hour exposure period, however it is important to ensure that the adherence of bacteria does not increase over 24 hours.

As shown in FIG. 3a, the ultimate reduction of attachment onto the chitosan/Cu-BTTri films is retained over the 24-hour period, with an 82-86% reduction observed. Indeed, this is a substantial reduction to achieve given the bacteria strain of P. aeruginosa. In contrast, the reduction was not maintained for the chitosan films, with only 33-43% reduction of attachment remaining after 24 hours. If the chitosan/Cu-BTTri films are again compared to the chitosan films themselves as the positive control, a 75-79% reduction in bacterial attachment onto chitosan/Cu-BTTri films is observed. All results determined by the CellTiter Blue assay were supported by enumerating the number of bacterial colonies on the films or wells using a sonication and plating assay. This technique removes the viable bacteria from the surface by sonicating for 30 minutes to liberate the attached bacteria as the planktonic form, which can then be serial diluted and agar plated to ultimately determine the number of colony-forming units (CFUs). Again, the determined CFUs were normalized by the given attachment area of the wells or films.

In addition, the number of colony-forming units (CFUs) that remained on each 10% film or well after the exposure period was determined using a sonication and plating method. The bacteria solution was removed from all wells, the wells were washed one time with warmed NBM, films were transferred to new wells, and fresh NBM was added to all wells. The plate was then sonicated for 30 minutes to remove the viable bacteria from the films or wells and 100 µL aliquots were serial diluted and 50 µL was plated on agar. The agar plates were placed in a static 37° C. incubator overnight and CFUs were counted the following morning. The amount of attached bacteria identified using this method was normalized by the area of the films or wells. (n=6)

Reusability of Chitosan and Chitosan/Cu-BTTri Films

The chitosan and 10% chitosan/Cu-BTTri films were saved after completing the initial round of attachment studies to determine if a similar reduction in attachment could be seen with the sterilized films. This was done by sterilizing the films in ethanol overnight and then allowing them to rehydrate in water before performing the CellTiter Blue assay again. This assay was performed in an identical fashion to initial bacterial attachment studies using CellTiter Blue and a 6- and 24-hour exposure period without the 72-hour NBM soaking period. (n=6)

Figure 3B:
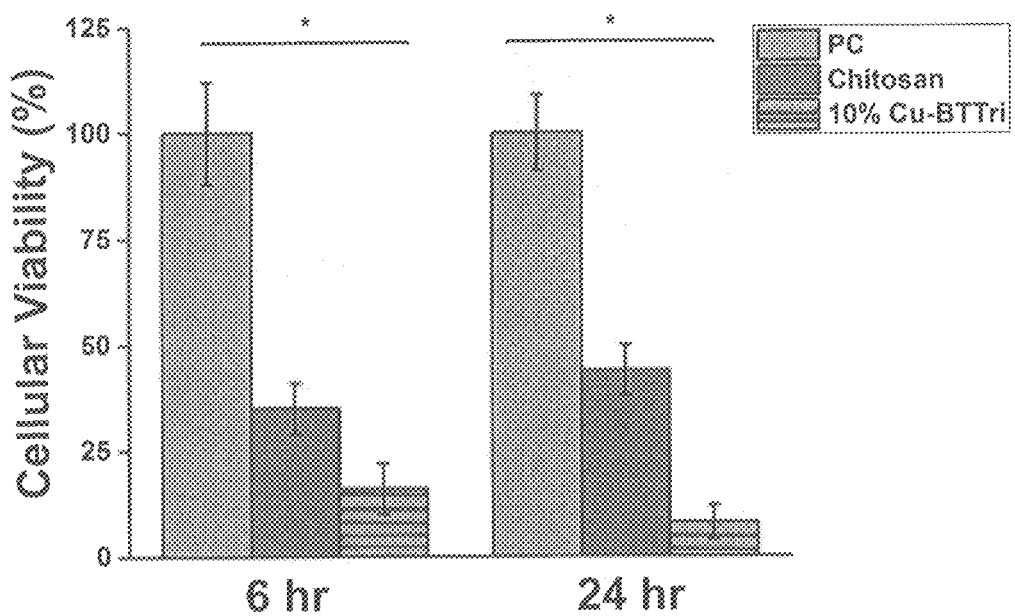

FIG. 3b shows the results of this study, where it is seen that a similar reduction in attachment is seen for all samples and both time points for the CellTiter Blue assay. Indeed, the bacteria cellular viabilities found for chitosan and chitosan/Cu-BTTri in the second round of assays is not statistically different from those determined from the first round of assays at a 95% confidence level. This observed continued function of the films demonstrates the usefulness and potential reusability of these novel materials to be used as biomaterials for antibacterial applications. This also suggests that the films may indeed be considered as passive antibacterial surfaces, as there is no loss of functionality after initial exposure to bacteria.

Previous reports of P. aeruginosa bacterial adhesion onto a surface vary widely with regards to the percent reduction observed. An example of an approach where an antimicrobial agent is released (in this case, nitric oxide) has been shown to inhibit P. aeruginosa attachment by 50-65% depending on the nitric oxide flux from the material. Another approach where contact killing is employed through the use of cationic peptides immobilized on a surface achieved up to 80% inhibition of P. aeruginosa. Finally, Hook et al. employed a passive approach for bacterial adhesion by implementing a novel material containing a combination of polymers to ultimately achieve ~80% reduction in P. aeruginosa attachment. These examples highlight the significant reduction achieved in this work using the chitosan/Cu-BTTri materials, where an ~85% reduction in achieved within the first 6 hours, maintained over 24 hours, and have the capabilities to achieve the same reduction again after the initial round of experiments.

Bacteria Control Studies (10% Chitosan/Cu-BTTri Films)

Due to potential antimicrobial effects from possible leachates from the chitosan/Cu-BTTri films (namely copper ions), a number of control studies were performed using P. aeruginosa both in solution and on the films themselves. Results from ICP-AES revealed that, for the 10% wt/wt films, 0.0725 f 0.0024 mg Cu/L NBM was present in the solutions after 72 hours of soaking in NBM at 37° C., representing ~2.5% of the total theoretical amount of copper in each film. To determine if this amount had any bactericidal effects on *P. aeruginosa*, an equivalent amount was introduced to the bacteria in NBM and exposed for 24 hours. The results indicated that there was no statistical difference between the cellular viability of the bacteria exposed to this concentration of copper and that of the control wells. Future attachment experiments were performed only after the 72-hour soaking period to ensure this amount of copper was not present during attachment assays, however this still provides insight into the mechanism of action for Cu-BTTri, indicating that these levels of copper would not explain the observed effect. This concept was also tested using triazole ligand (1,3,5-tris(1H-1,2,3-triazol-5-yl)benzene) in powder form at the same amount that would be present in the chitosan/Cu-BTTri films (0.055 mg triazole mg$^{-1}$ chitosan/Cu-BTTri film). This amount of ligand was exposed to *P. aeruginosa* for 24 hours and the resulting bacteria solution was tested for cellular viability using the CellTiter Blue assay. Results from this were similar to the copper ion experiment, where there was no observed decrease in bacteria viability after exposure to triazole compared to the positive control. Finally, a metal ion chelator that displays selectivity for copper ions (Chelex-100 Resin) was added to the bacterial solution in the presence of the chitosan/Cu-BTTri films to remove any labile or weakly associated copper ions that may be contributing to the observed effect. There was no statistical difference in the amount of viable bacteria attached to the films in the absence or presence of the metal ion chelator, further giving insight into the mechanism of inhibition arising from the intact Cu-BTTri within the chitosan matrix. An initial control experiment was also conducted using the metal chelator in the presence of bacteria only to ensure the Chelex-100 did not compromise the integrity of healthy bacteria cells.

In addition to testing the individual components of the MOF for antibacterial activity, the surrounding bacterial solution can also be tested for cellular viability in addition to quantifying the attached bacteria onto the films. This does not test individual components of potential leachates (as was the case for copper ions and triazole powder), but rather assesses the entire film solution for presence of any antibacterial agents. For this assay, aliquots of the bacteria solution surrounding the films (both chitosan and chitosan/Cu-BTTri) were mixed with the CellTiter Blue reagent to determine cellular viability. Likewise to the copper ion and triazole assays, there was no decrease in bacteria viability observed for either film (chitosan or chitosan/Cu-BTTri) when compared to the positive control. This ensures that leachates do not occur at sufficient concentration to compromise the integrity of healthy bacteria, further demonstrating the localized effect of the film on bacteria rather than the release of antibacterial agents. A summary of the control experiments and subsequent results can be found in Table 2, in which *P. aeruginosa* was used with chitosan and 10% wt/wt chitosan/Cu-BTTri film components for cellular viability by CellTiter Blue assay (Y=yes; N=no). (n≥3).

TABLE 2

| Sample | >80% Reduction in Viable Bacteria in 6 hours | >80% Reduction in Viable Bacteria in 24 hours |
|---|---|---|
| Chitosan/Cu-BTTri | Y | Y |
| Chitosan | N | N |
| Copper ions | N | N |
| Triazole powder | N | N |
| Bacterial solution | N | N |

Figure 4:
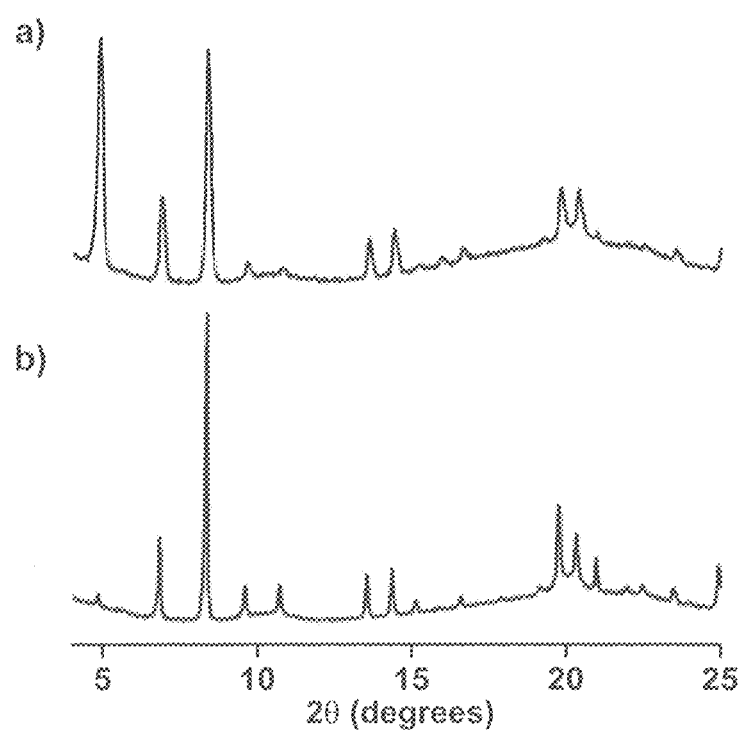
FIG. 4 shows pXRD diffraction patterns of chitosan/Cu-BTTri film prior to and following a bacterial assay according to some embodiments.

In order to confirm that Cu-BTTri remained intact following the bacterial attachment studies, the structural integrity of the chitosan/Cu-BTTri films was assessed by performing pXRD on the samples. FIG. 4 shows the results of this analysis, where (a) is the pXRD diffraction pattern of chitosan/Cu-BTTri films prior to beginning the bacterial assays and (b) is the pXRD diffraction pattern after the bacterial assays were performed. The key peaks associated with the MOF after the bacterial assays match those found from films prior to beginning the bacterial attachment experiments. This provides further indication that the Cu-BTTri remains crystalline and intact throughout the attachment experiments.

Additional details of the bacterial attachment studies follow. The bactericidal activity of the bacterial attachment solution was determined by removing an aliquot of the bacteria solution after the exposure period and tested for bacteria cellular viability using the CellTiter Blue assay. (n=6) The bactericidal activity of the average amount of copper in solution from the chitosan/Cu-BTTri films (as found by ICP-AES) was determined by exposing that amount of copper (in the form of copper chloride) to the *P. aeruginosa* bacterial solution for 24 hours. The mass of copper chloride was added to the bacteria solution in NBM and stored at 37° C. After 24 hours, 100 µL aliquots of the control wells (equal volume of NBM without added copper chloride) and the copper sample wells were combined with 300 µL CellTiter Blue solution. The wells were analyzed in a similar fashion to the CellTiter Blue attachment assay for bacteria cellular viability. (n=3)

The average amount of triazole present in the chitosan/Cu-BTTri films was exposed to *P. aeruginosa* bacteria solution in a similar fashion to the copper chloride solution to test for antibacterial activity. Briefly, the average mass of triazole powder was introduced to the bacteria solution in NBM for a 24-hour exposure period. Aliquots of the remaining bacterial solution were combined with CellTiter Blue solution and the cellular viability was assessed by comparing the wells containing triazole to the wells containing NBM only. The triazole powder in the absence of bacteria was also tested using the CellTiter Blue solution as a negative control to ensure the triazole did not adversely affect the CellTiter Blue reagent. (n=3)

Control studies were also performed using chitosan films with copper chelated to the chitosan. These films were soaked for either 24 or 72 hours in NBM at 37° C. and the resulting soaking solution was exposed to *P. aeruginosa* bacteria solution. The CellTiter Blue assay was performed on the bacteria solution after 24-hour exposure time and the copper-chitosan soaking solutions were compared to a positive control of bacteria solution only. (n=4)

The metal chelator Chelex-100 Resin (1-2 mg) was added to wells containing the 10% chitosan/Cu-BTTri films before performing the 6- and 24-hour attachment studies. An equivalent amount of Chelex-100 Resin was also added the bacterial solution in the absence of the films as an additional control study. (n=3)

Impact of Varying Cu-BTTri Concentration

Figure 5:
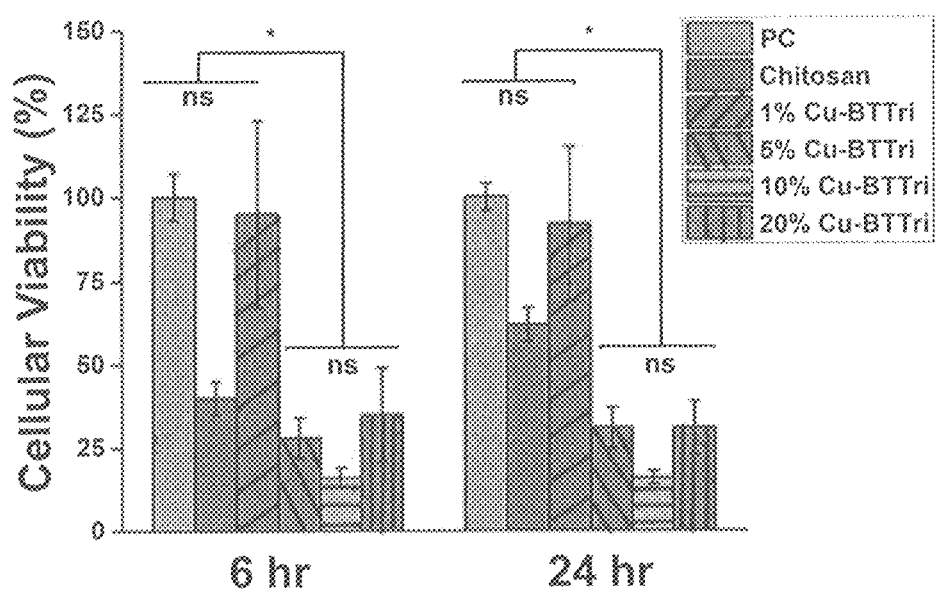
FIG. 5 is a bar chart reporting cellular viability after 6 hours and 24 hours of exposure according to some embodiments.

In order to determine the threshold for the observed reduction in bacterial attachment, a range of MOF compositions were tested, yielding 1%, 5%, 10%, and 20% wt/wt Cu-BTTri incorporation. FIG. 5 displays the results of this assay for all film compositions, with the polystyrene well again used as the positive control. Average and 95% confidence interval are displays. Statistically significant differences between cellular viabilities are indicted (*) and not statistically significant differences are indicated by (ns) as determined by a one-way ANOVA.

After 6 hours of exposure to bacteria, the reduction in attachment observed between the chitosan films and the 1% chitosan/Cu-BTTri films are not statistically different. Likewise, the films containing additional incorporation of the MOF (5% and 20% wt/wt) display no statistical difference observed for all values of cellular viability when compared to the 10% films. After 24 hours exposure to bacteria, the chitosan and the 1% Cu-BTTri films show no statistical difference in reduction, while the 5% and 20% films are comparable to what was observed for the original 10% films. Based on these findings using a variety of MOF compositions, it can be seen that the threshold for biofilm inhibition begins with the 5% wt/wt incorporation, and the desired function does not increase as more Cu-BTTri is incorporated into the chitosan matrix (as seen with both 10% and 20% wt/wt).

Cumulative amount of copper in solution (as percent copper in solution relative to total copper content of films) in soaking solutions of 1%, 5%, 10%, and 20% wt/wt chitosan/Cu-BTTri films after 72 hours are presented in Table 3. Soaking studies were performed in NBM at 37° C. over three 24-hour periods. Data presented as average±standard deviation, n=3.

TABLE 3

| Cu-BTTri incorporation (% wt/wt) | Copper in solution after 24 h (% original Cu content) | Copper in solution after 48 h (% original Cu content) | Copper in solution after 72 h (% original Cu content) |
| --- | --- | --- | --- |
| 1 | 0.10 ± 0.03 | 0.36 ± 0.25 | 0.76 ± 0.45 |
| 5 | 0.48 ± 0.27 | 0.96 ± 0.35 | 1.69 ± 0.69 |
| 10 | 1.85 ± 0.52 | 2.25 ± 0.57 | 2.47 ± 0.59 |
| 20 | 0.22 ± 0.07 | 0.52 ± 0.12 | 0.83 ± 0.33 |

The extensive control studies performed using the 10% wt/wt chitosan/Cu-BTTri films gives insight into the factors that do not influence the observed antibacterial nature of the films. By ensuring that the bacterial solution above the films is not adversely affected compared to the positive control, it can be concluded that leachates from the films are not acting in an antibacterial fashion. Additionally, it would appear that any labile copper ions not directly coordinated within the material framework are not responsible for the inhibition of bacterial attachment, as the chelator control experiment would have removed those copper ions from solution. Finally, demonstrating the observed effect for the incorporated Cu-BTTri at different weight percent's would indicate that there is an upper and lower limit to the amount of incorporated MOF necessary to elicit the desired response. When adding only 1% wt/wt Cu-BTTri, there was no statistical difference observed between the chitosan and chitosan/Cu-BTTri with regard to their inhibition properties. Conversely, increasing the incorporated Cu-BTTri from 5% to 10% and 20% wt/wt did not increase the observed antibacterial nature, suggesting a saturation point to the activity imparted onto the bacteria.

A significant reduction (~85%) in bacterial attachment was demonstrated using a water-stable MOF blended with chitosan. This inhibition is considered substantial in the field of novel antibacterial surfaces, particularly noteworthy for the bacteria strain *P. aeruginosa* which is known to be a robust biofilm former. Characterization by ATR-IR and pXRD confirm the structural integrity of the MOF before and after blending into chitosan films. Chitosan/Cu-BTTri blended films were utilized for bacterial attachment inhibition properties by testing the activity against *P. aeruginosa* over 6- and 24-hour periods. The biofilm inhibition of *P. aeruginosa* was observed for the 5, 10, and 20% wt/wt blended films after 6 hours and was maintained for the entire 24-hour challenge period. This functionality was retained after a second round of bacterial attachment studies, suggesting reusability of these materials as antibacterial surfaces. Finally, extensive control assays were performed to differentiate this observed antibacterial effect to the previous antibacterial publications for copper-based MOFs where the proposed mechanism is the slow, continuous release of copper ions. These control studies allow us to isolate the observed biological effects to the chitosan/Cu-BTTri film itself and not to possible leachates from films during experiments. This material presents an opportunity for a novel biomaterial to be utilized as a passive antibacterial surface in settings with prevalent bacterial infections to serve as a biofilm inhibitor.

Various modifications and additions can be made to the exemplary embodiments discussed without departing from the scope of the present invention. For example, while the embodiments described above refer to particular features, the scope of this invention also includes embodiments having different combinations of features and embodiments that do not include all of the above described features.

The following is claimed:

1. A method of reducing adhesion of bacteria on a surface of a substrate, the method comprising:
    forming the surface of the substrate from a material comprising water-stable copper-based metal-organic frameworks dispersed throughout a water-insoluble chitosan matrix, wherein the copper-based metal-organic frameworks are present in an effective amount such that after six hours of exposure to a solution containing the bacteria, bacterial adhesion of the bacteria on the surface is reduced as compared to a surface not containing the material and wherein after six hours of exposure to the solution the material did not release copper in a bactericidal effective amount in the solution.

2. The method of claim 1 wherein the bacteria is *Pseudomonas aeruginosa*.

3. The method of claim 1 wherein the water-stable copper-based metal-organic frameworks are present in amount of 5% wt/wt to 20% wt/wt based on total solids of the water-stable copper-based metal-organic frameworks and the water-insoluble chitosan matrix.

4. The method of claim 1 wherein the water-stable copper-based metal-organic frameworks are present in amount of 5% wt/wt based on total solids of the water-stable copper-based metal-organic frameworks and the water-insoluble chitosan matrix.

5. The method of claim 4 wherein water-stable copper-based metal-organic frameworks are $H_3[(Cu_4Cl)_3\text{-}(BTTri)_8]$ ($H_3BTTri=1,3,5\text{-tris}(1H\text{-}1,2,3\text{-triazol-5-yl})$benzene).

6. A method of reducing adhesion of bacteria on a surface of a substrate, the method comprising:

exposing the substrate comprising water-stable copper-based metal-organic frameworks dispersed throughout a water-insoluble chitosan matrix on the surface to a solution containing the bacteria, wherein the copper-based metal-organic frameworks are present in an effective amount such that after six hours of exposure to the solution, bacterial adhesion on the surface is reduced as compared to a surface not containing the copper-based metal-organic frameworks dispersed throughout the chitosan matrix and wherein after six hours of exposure to the solution the substrate did not release copper in a bactericidal effective amount in the solution.

7. The method of claim 6 wherein the bacteria is *Pseudomonas aeruginosa*.

8. The method of claim 6 wherein the water-stable copper-based metal-organic frameworks are present in amount of 5% wt/wt to 20% wt/wt based on total solids of the water-stable copper-based metal-organic frameworks and the water-insoluble chitosan matrix.

9. The method of claim 6 wherein the water-stable copper-based metal-organic frameworks are present in amount of 5% wt/wt to 10% wt/wt based on total solids of the water-stable copper-based metal-organic frameworks and the water-insoluble chitosan matrix.

10. The method of claim 6 wherein the water-stable copper-based metal-organic frameworks are present in amount of 5% wt/wt based on total solids of the water-stable copper-based metal-organic frameworks and the water-insoluble chitosan matrix.

11. The method of claim 6 wherein water-stable copper-based metal-organic frameworks are H3[(Cu4Cl)3-(BTTri)8] (H3BTTri=1,3,5-tris(1H-1,2,3-triazol-5-yl)benzene).

* * * * *